United States Patent
Kratz et al.

[11] Patent Number: 5,952,438
[45] Date of Patent: Sep. 14, 1999

[54] POLYMERIC POLYAMINES FROM ALTERNATING POLYKETONES

[75] Inventors: Detlef Kratz, Heidelberg; Ferdinand Lippert; Peter Schwab, both of Bad Dürkheim; Dieter Boeckh, Limburgerhof; Johannes Perner, Neustadt, all of Germany

[73] Assignee: BASF Aktiengesellschaft, Ludwigshafen, Germany

[21] Appl. No.: 08/992,530

[22] Filed: Dec. 17, 1997

[30] Foreign Application Priority Data

Dec. 23, 1996 [DE] Germany .................. 196 54 058

[51] Int. Cl.⁶ ............................................ C08G 73/02
[52] U.S. Cl. ................... 525/471; 525/342; 525/378; 525/379; 525/380
[58] Field of Search ................... 525/471, 378, 525/379, 380, 342

[56] References Cited

U.S. PATENT DOCUMENTS 2,495,255  1/1950  Hoehn .............................. 260/63

*Primary Examiner*—Frederick Krass
*Attorney, Agent, or Firm*—Keil & Weinkauf

[57] ABSTRACT

Polymeric polyamines obtainable by reacting linear, alternating carbon monoxide/1-alkene copolymers with ammonia or amines of the formula (I)

$$R-NH_2 \qquad (I)$$

where R is $-NH_2$, $-OH$, $C_1-C_{10}$-alkyl, $C_6-C_{20}$-aryl, $C_7-C_{20}$-arylalkyl, $C_7-C_{20}$-alkylaryl or an organosilicon radical having 3 to 30 carbon atoms, or with a reagent which releases ammonia or the amine (I), and subsequent hydrogenation.

5 Claims, No Drawings

POLYMERIC POLYAMINES FROM ALTERNATING POLYKETONES

The present invention relates to polymeric polyamines obtainable by reacting linear, alternating carbon monoxide/1-alkene copolymers with ammonia or amines of the formula (I)

R—NH$_2$       (I)

where R is —NH$_2$, —OH, C$_1$–C$_{10}$-alkyl, C$_6$–C$_{20}$-aryl, C$_7$–C$_{20}$-arylalkyl, C$_7$–C$_{20}$-alkylaryl or an organosilicon radical having 3 to 30 carbon atoms,
or with a reagent which releases ammonia or the amine (I), and subsequent hydrogenation, to a process for preparing polymeric polyamines by reacting carbon monoxide/1-alkene copolymers with ammonia or amines of the formula (I)

R—NH$_2$       (I)

where R is —NH$_2$, —OH, C$_1$–C$_{10}$-alkyl, C$_6$–C$_{20}$-aryl, C$_7$–C$_{20}$-arylalkyl, C$_7$–C$_{20}$-alkylaryl or an organosilicon radical having 3 to 30 carbon atoms,
or with a reagent which releases ammonia or the amine (I), and subsequent hydrogenation, and to the use of the polymeric polyamines as surfactants, dispersant, paper auxiliary, soil remover, component in skin creams and hair care, crosslinker for adhesives, stabilizer for polyoxymethylene, corrosion inhibitors, textile assistant, auxiliary for dispersions, adhesives, protective colloids, adhesive coating, epoxy hardener in aqueous dispersions, auxiliary for dishwashing compositions, leveling agent for textiles, solubilizer for cosmetics, auxiliary for metal extraction, complexing agent, fuel additive, lubricants, corrosion inhibitor for aqueous systems, addition to size and resin raw materials, auxiliary for dye fixation on textiles, auxiliary in paper fixing, retention aid, complexing agent for metal recycling, stabilizers for hydroxylamine, or color transfer inhibitors.

Polymeric polyamines are important auxiliaries for example in the paper or detergent industry. They are generally obtained by polymerizing nitrogen-containing monomers. The properties of the currently available polymeric polyamines are, as a rule, determined by the structure and reactivity of the monomers and must be adapted to diverse purposes of use. The small number of commercially available nitrogen monomers means that this adaptation is possible only with limitations. The properties of the polymer are normally determined not only by the N/C ratio but also by the nature of the N functionality. Thus, it is desirable to influence the molar ratio of primary, secondary or tertiary N functionalities.

It is an object of the present invention to provide polymeric polyamines with varying properties and a relatively large proportion of amine groups, if possible by means of a variable process.

We have found that this object is achieved by the polymeric polyamines obtainable by reacting linear, alternating carbon monoxide/1-alkene copolymers with ammonia or amines of the formula (I)

R—NH$_2$       (I)

where R is —NH$_2$, —OH, C$_1$–C$_{10}$-alkyl, C$_6$–C$_{20}$-aryl, C$_7$–C$_{20}$-arylalkyl, C$_7$–C$_{20}$-alkylaryl or an organosilicon radical having 3 to 30 carbon atoms,
or with a reagent which releases ammonia or the amine (I), and subsequent hydrogenation, and by a process for preparing polymeric polyamines by reacting carbon monoxide/1-alkene copolymers with ammonia or amines of the formula (I)

R—NH$_2$       (I)

where R is —NH$_2$, —OH, C$_1$–C$_{10}$-alkyl, C$_6$–C$_{20}$-aryl, C$_7$–C$_{20}$-arylalkyl, C$_7$–C$_{20}$-alkylaryl or an organosilicon radical having 3 to 30 carbon atoms,
or with a reagent which releases ammonia or the amine (I), and subsequent hydrogenation, using linear alternating carbon monoxide/1-alkene copolymers. We have furthermore found the use of the polymeric polyamines defined at the outset inter alia as surfactants and dolor transfer inhibitors.

Linear, alternating carbon monoxide/1-alkene copolymers (alternating polyketones) underlying the polymeric polyamines are known and can generally be obtained by palladium-catalyzed copolymerization of carbon monoxide with a 1-alkene or a plurality of 1-alkenes. As a rule they have the following repeating unit.

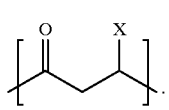

II

In this, X is hydrogen, C$_1$–C$_{10}$-alkyl, such as methyl, ethyl, n-propyl, isopropyl, n-butyl, tert-butyl, n-hexyl, n-octyl or n-decyl, but preferably hydrogen or methyl. The linear alternating copolymers thus also include polymers with more than one type of structural units derived from 1-alkene, such as carbon monoxide/ethylene/propene terpolymers. The carbonyl group:alkylene structural unit molar ratio in the alternating polyketones is normally 1:1. The average molecular weight Mn of the linear, alternating carbon monoxide/1-alkene copolymers, determined by the NMR spectroscopic method, is normally in the range from 100 to 1,000,000, preferably in the range from 150 to 500,000, in particular in the range from 100 to 50,000.

The novel polymeric polyamines can be obtained by reacting the described linear, alternating carbon monoxide/1-alkene copolymers with ammonia, amines of the formula R—NH$_2$ (I) or with a reagent which releases ammonia or the amines (I), and subsequent hydrogenation.

Suitable R radicals in (I) are —NH$_2$, —OH, C$_1$–C$_{10}$-alkyl such as methyl, ethyl, n-propyl, i-propyl, n-butyl, sec-butyl, isobutyl, tert-butyl, n-hexyl, n-octyl, n-decyl, and furthermore C$_6$–C$_{20}$-aryl such as phenyl, naphthyl, C$_7$–C$_{20}$-arylalkyl such as benzyl and C$_7$–C$_{20}$ alkylaryl such as p-tolyl, o-tolyl, xylyl. Further suitable R radicals in (I) are organosilicon radicals having 3 to 30 carbon atoms, thus tri(C$_1$–C$_{10}$ alkyl)silyl such as trimethylsilyl, tert-butyldimethylsilyl or else triarylsilyl, for example triphenylsilyl, tri-p-tolylsilyl or trinaphthylsilyl.

Generally suitable reagents releasing ammonia are all ammonium salts, preferably ammonium carbonate, ammonium acetate and ammonium formate.

Preferably used as aminating reagent is ammonia, hydrazine or ammonium carbonate, where appropriate in the form of the hydrates. Ammonia is very particularly preferred. Ammonia, the amines (I) or the reagents releasing the ammonia or the amines (I), called aminating reagents hereinafter, can be used as pure substances or dissolved in organic solvents such as tetrahydrofuran, dioxane, toluene, N-methylpyrrolidone or water or mixtures thereof.

The aminating reagents can be used either in excess or in the stoichiometric or less than stoichiometric amount, in each case based on the carbonyl group >C═O in the linear, alternating carbon monoxide/1-alkene copolymers.

The preferred reaction of the linear alternating carbon monoxide/1-alkene copolymers with stoichiometric amounts or an excess of ammonia normally results, after hydrogenation, in polymeric polyamines with a primary amine functionality: (total of secondary amine functionality and tertiary amine functionality) molar ratio in the range from 1:1 to 1:10,000, preferably 1:2 to 1:100. The amine values, on which these ratios are based, are determined by titration as described in the examples.

It is assumed on the current state of knowledge the following structural units III may be present in the polymeric polyamines obtainable in this way, with the structural units indicated by the indices a,b and c usually being distributed randomly along the polymer chain.

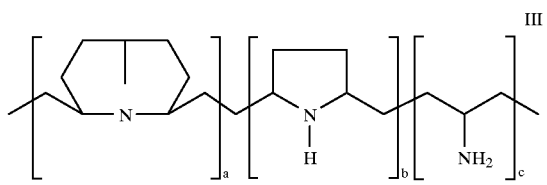

III

Particularly good results are usually achieved when the aminating reagent:polyketone carbonyl group molar ratio is in the range from 1.1:1 to 20:1 or is, in particular, 2:1.

Polymeric polyamines obtainable with stoichiometric amounts or with an excess of aminating reagents generally comprise less than 5% by weight carbonyl groups >C═O based on the polymeric polyamine, determined by the $^{13}$C-NMR spectroscopic method in CDCl$_3$, at 20° C., and less than 10% by weight, preferably less than 1% by weight, hydroxyl groups, based on the polymeric polyamine.

If the aminating reagents are used in less than stoichiometric amounts, preferably in amounts in the range from 0.01 to 0.99, based on the carbonyl functionality >C═O in the polyketone, the resulting polymeric polyamines generally comprise an ether functionality, as 2,5-tetrahydrofurandiyl unit, detected by the $^{13}$C-NMR spectroscopic method, and hydroxyl groups. The amounts and molar ratios of the functional nitrogen and oxygen groups in the polymeric polyamine normally depend on the reaction conditions in the preparation thereof using less than stoichiometric amounts of aminating reagents. The total amount of chemically bonded oxygen in the polymeric polyamine:total amount of chemically bonded ether and hydroxyl oxygen in the polymeric polyamine molar ratio is normally in the range from 1:1000 to 1000:1, preferably in the range from 1:100 to 100:1.

In the particularly preferred reaction of less than stoichiometric amounts of ammonia, preferably in amounts in the range from 0.1 to 0.99, based on the carbonyl functionality >C═O, with the linear alternating carbon monoxide/1-alkene copolymers, preferably carbon monoxide/ethylene copolymers, the resulting polymeric polyamines generally comprise, in addition to the primary, secondary and tertiary amine functionalities already described, an ether functionality, as 2,5-tetrahydrofurandiyl unit, and hydroxyl groups. The amounts and molar ratios of the functional nitrogen and oxygen groups in the polymeric polyamine also normally depend in this instance on the reaction conditions in the preparation of the polymeric polyamines using less than stoichiometric amounts of ammonia. The total amount of chemically bonded oxygen in the polymeric polyamine::total amount of chemically bonded ether and hydroxyloxygen in the polymeric polyamine molar ratio is normally in the range from 1:1000 to 1000:1, preferably in the range from 1:100 to 100:1. The primary amine functionality: (secondary amine functionality+tertiary amine functionality) molar ratio in the polymeric polyamine is normally in the range from 1:1 to 1:10,000, preferably in the range from 1:2 to 1:100.

The polymeric polyamines obtainable with less than stoichiometric amounts of aminating reagents generally comprise less than 5% by weight, preferably less than 3% by weight, carbonyl groups >C═O, based on the polymeric polyamine, determined by the $^{13}$C-NMR spectroscopic method in CDCl$_3$ as solvent at 20° C.

The number average molecular weight Mn determined by the gel permeation chromatography method of the novel polymeric polyamines is generally in the range from 100 to 1,000,000, preferably in the range from 100 to 500,000 and in particular in the range from 100 to 50,000.

A suitable process for preparing the polymeric polyamines is to react the linear alternating carbon monoxide/1-alkene copolymers defined at the outset with ammonia or the amines R—NH$_2$ (I) already defined, or with a reagent which releases ammonia or the amines (I) already defined, and subsequent hydrogenation.

A two-stage process has proven particularly suitable, in the first stage of which the linear alternating carbon monoxide/1-alkene copolymers are reacted with ammonia or the amines R—NH$_2$ (I) already defined or with a reagent releasing ammonia or the amines (I) normally at from 20 to 250° C., preferably from 50 to 150° C., under a pressure of from 100 to 20,000 kPa, without diluent or in water or organic solvents such as tetrahydrofuran, dioxane, toluene, N-methylpyrrolidone or cyclohexane. The hydrogenation is then carried out in a second stage, preferably without isolating and working up the reaction products from the first stage, generally in the presence of a hydrogenation catalyst under a pressure of hydrogen in the range from 100 to 35,000 kPa, preferably 1000 to 25,000 kPa, at from 20 to 250° C., preferably from 100 to 220° C.

Suitable as hydrogenation catalyst are all those described for this purpose in D. D. Coffmann, J. Am. Chem. Soc. 76 (1954), 25 6394–6399; A. Sen, Adv. Polym. Sci. (1986) 125–144, but nickel (14% by weight)/aluminum oxide, ruthenium (0.5% by weight)/macroporous aluminum oxide or ruthenium oxide hydrate is preferably used.

The amination and the hydrogenation are normally carried out until at least 5 mol % of the carbonyl groups >C═O in the initial polyketone have reacted, which can be checked by infrared spectroscopy. Preferred reaction times, both for the amination and for the hydrogenation, are in the range from 0.5 to 20 hours.

The aminations can, as described above, be carried out with an excess or with stoichiometric amounts or less than stoichiometric amounts of aminating reagent, preferably ammonia, based on the carbonyl group >C=O in the linear alternating carbon monoxide/1-alkene copolymers.

The novel polymeric polyamines can also be modified by conventional chemical methods. For example, the ammonium salts result from the reaction with acids such as carboxylic acids, ie. acetic acid, trifluoroacetic acid or else inorganic acids, such as sulfuric acid, hydrochloric acid or phosphoric acid.

The novel polymeric polyamines can furthermore be alkylated with $C_1$–$C_{25}$-alkylating agents such as dialkyl sulfates, preferably dimethyl sulfate or diethyl sulfate, or else alkyl halides such as benzyl chloride. Generally used for this purpose are 0.1 to 2 mole equivalents, preferably 1 to 2 mole equivalents, of alkylating agent, based on the amine groups present in the polymer. Reaction of the novel polymeric polyamines with alkylene oxides, preferably ethylene oxide or propylene oxide, normally results in the corresponding alkoxylates, eg. ethoxylates.

The novel polymeric polyamines are very suitable as surfactants and, in particular, as color transfer inhibitors, especially in detergents.

The novel polymeric polyamines are particularly suitable for detergents and fabric conditioners which are free of anionic surfactants and those which have an anionic surfactant content of less than 2.5%, preferably less than 1.5%, particularly preferably 0 to 1%, of anionic surfactants.

In a formulation free from anionic surfactants, the novel polymeric polyamines normally reach the effect plateau at a concentration of only 20 to 100 ppm in the wash or rinse liquor, whereas prior art polymers are used in concentrations of about 500 ppm.

The novel polymeric polyamines are generally used in the fabric conditioners or detergents in amounts of from 0.05 to 10%, preferably 0.1 to 5.0%, particularly preferably 0.2 to 2.5%, based on the other ingredients of the formulation.

The novel polymeric polyamines can advantageously be used as addition to liquid or solid detergent formulations or fabric conditioners which have a low or zero content of anionic surfactants. The composition of detergents and fabric conditioners can moreover be varied within wide limits.

EXAMPLES

A) $^1$H-NMR spectroscopic determination of the average molecular weight $M_n$ of polyketone To determine the molecular weight $M_n$, a $^1$H-NMR spectrum was recorded (D1=20 sec; NS=3000) on a concentrated sample of polyketone dissolved in hexafluoroisopropanol:d6-benzene (90:10) under quantitative conditions.

$$CH_3-CH_2-\underset{\underset{O}{\parallel}}{C}-(CH_2-CH_2-C)_x\ CH_2-CH_2-\underset{\underset{O}{\parallel}}{C}-O-CH_3$$
$$1\quad 3\quad 2\quad\quad 3\quad\ 3\quad 4\quad\quad 3\quad\ 5\quad 6\quad\ 7$$

The molecular weight can be calculated from the integrated intensities of signals 1, 3 and 5 (and possibly 7).

Firstly, the average of the integrated intensities of signals 1 and 5 was formed (one carbon atom corresponds to x mm).

Then the integrated intensities of signal 3 (—$CH_2$—$CH_2$—)$_x$ were divided by the average of C— of the end group. The resulting number of $CH_2$ groups was divided by 2 (minus one unit=2$CH_2$ from end groups) to result in the $CH_2$—$CH_2$—C=O units.

The number of units was multiplied by the molecular weight (~56) for one unit. The molecular weight for the two end groups $$(CH_3-CH_2-\underset{\underset{O}{\parallel}}{C}-\quad\text{and}\quad CH_2-CH_2-\underset{\underset{O}{\parallel}}{C}-O-CH_3\quad\sim144\ MW)$$

was added on.

The result corresponded to the average molecular weight.

B) Determination of the total nitrogen base content

About 150 mg of the sample were weighed accurately and dissolved in 50 ml of glacial acetic acid. This solution was titrated potentiographically with a 0.1 mol/l trifluoromethanesulfonic acid volumetric solution to the turning point.

The total percentage nitrogen base content was calculated by the following formula:

$$w=c.t.M.0.1.(v1-v2)/(m.z)$$

where c=molar concentration of the trifluoromethanesulfonic acid solution, t=titer of the trifluoromethanesulfonic acid solution M=atomic mass of nitrogen (14.01 g/mol)

v1=volume in ml of trifluoromethanesulfonic acid used for the sample v2=volume in ml of trifluoromethanesulfonic acid used for the blank sample m=sample weight in g z=equivalent number C) Determination of tert. amine About 150 mg of sample were weighed accurately, dissolved in 20 ml of acetic acid and 30 ml of acetic anhydride and heated at 70° C. for 2 h. After cooling, the solution was titrated potentiographically with a 0.1 mol/l trifluoromethanesulfonic acid solution to the first turning point.

The percentage tert. amine content was calculated as described under B).

D) Determination of prim. amine

About 1.5 g of the sample were dissolved in 5 ml of pyridine and, after addition of 5 ml of acetylacetone, stirred at room temperature for 2 hours. Then 40 ml of pyridine and 10 ml of methanol were added, and the solution was titrated potentiographically with a 1 mol/l sodium methoxide solution to the turning point.

The percentage prim. amine content was calculated as described under B).

E) Calculation of sec. amine

The total of the figures determined for tert. amine and prim. amine as described in C) and D) was subtracted from the total nitrogen base content.

Example 1

Preparation of an alternating polyketone

Methanol, palladium acetate, bis(di-tert-butylphosphino) methane and p-toluenesulfonic acid were introduced into a 0.3 l autoclave. Then, at the selected reaction temperature, a mixture of ethylene and carbon monoxide in the molar ratio 1:1 was injected to a total pressure of 60 bar. The temperature and partial pressures of the monomers were kept constant throughout the reaction, after which the polymerization was stopped by decompressing the autoclave, and the solvent was filtered off.

The process parameters, amounts of catalyst and solvent used, and the amounts of copolymer obtained and its melting point are to be found in the table.

|  | Example 1 |
| --- | --- |
| Methanol [g] | 100 |
| Palladium acetate [mg] | 49 |
| Bisphosphine [mg] | 270 |
| p-Toluenesulfonic acid [mg] | 140 |
| Reaction temperature [° C.] | 85 |
| Reaction time [h] | 3 |
| Polyketone [g] | 43 |
| Melting point [° C.] | 237 |

Example 2

146 g of a polyketone of molecular weight Mn=2600 were suspended in 4000 g of THF in an autoclave with a volume of 10 l. 8 g of $RuO_2(H_2O)_6$ (water content 75%) were added. The autoclave was closed and, while stirring, 600 g of $NH_3$ were injected. The autoclave was then heated with stirring to 150° C., an autogenous pressure of 19 bar being set up. After 15 h, hydrogen was injected to 150 bar at the same temperature. The autoclave was then heated to 200° C., and hydrogen was injected to 250 bar. The reaction time was 20 h. The autoclave was cooled and decompressed, during which excess ammonia escaped. The pale yellow solution was filtered, and the THF and water which had formed were removed by distillation under reduced pressure. Oil pump drying resulted in 93 g of a honey-like oligomer.

Characteristic figures:

| C | H | N | O |
| --- | --- | --- | --- |
| 75.6 | 11.2 | 11.2 | 1.9 |

| primary N | [g/100 g] | 1.0 |
| --- | --- | --- |
| secondary N | [g/100 g] | 4.1 |
| tertiary N | [g/100 g] | 5.58 |
| total N | [g/100 g] | 10.69 |
| OH number | [mg KOH/g] | 35 |
| CO number | [mg KOH/g] | 59 |

Example 3 to 8

The reactions were carried out as in Example 2 but using polyketones whose chain length differed and different ratios of amounts. The conditions and results are summarized in Table 1.

Example 9 to 13

The reaction was carried out as in Example 2 but using a heterogeneous catalyst of Ru (0.5%) on $Al_2O_3$ in place of $RuO_2 (H_2O)_6$. This catalyst was immersed in a basket in the autoclave. The conditions and results are summarized in Table 2.

Example 14 to 16

The reaction was carried out as in Example 9 but using less than the stoichiometric amount of ammonia (Table 2).

Example 17

The reaction was carried out as in Example 14 but using 24 g of $(NH_4)_2CO_3$ in place of ammonia for amination of the 168 g of polyketone used (Table 2).

Example 18

100 g of reductively aminated polyketone from Example 10 were reacted with 5.5 equivalents of ethylene oxide (EO) at 150–155° C. The amount (218 g) found in the discharge corresponds to 97% of the precursors used (100 g of reductively aminated polyketone and 124 g of EO). Polyethylene glycols which had been formed were removed by extracting twice with diethyl ether. 197 g of oligomer remained. The characteristic figures (now only tert. N functionalities) demonstrate that there was complete addition to all N functionalities.

|  | Reductively aminated polyketone (Example 10) | Ethoxylate |
| --- | --- | --- |
| OH number (mg KOH/g) | 178 | 283 |
| CO number (mg KOH/g) | 3 | 3 |
| prim. N (g/100 g) | 0.3 | <0.1 |
| sec. N (g/100 g) | 6.3 | <0.1 |
| tert. N (g/100 g) | 4.51 | 5.59 |
| tot. N (g/100 g) | 11.15 | 5.5 |

Example 19

20 g of reductively aminated polyketone from Example 5 were dissolved in 169.5 g of aqueous sulfuric acid (0.5 M). The pH of the solution is 3. The solution was filtered, and the water was removed by distillation under reduced pressure to leave 29 g of a solid which is readily soluble in water and corresponds to the sulfate salt of the polymer.

Example 20

82 g of dimethyl sulfate dissolved in 82 g of toluene were added dropwise over the course of 1 h to a solution of 50 g of reductively aminated polyketone from Example 5 in 450 g of toluene at 50 to 70° C. The resulting brown solid was filtered off. Excess dimethyl sulfate was removed by dissolving the solid in water and extracting with diethyl ether. The aqueous phase was evaporated to leave 87 g of solid. The characteristic figures (see below) demonstrate that the reaction had quantitatively converted all primary, secondary and tertiary N atoms into quaternary N atoms.

|  | Reductively aminated polyketone (Example 2) | Quaternized product |
| --- | --- | --- |
| OH number (mg KOH/g) | n.d. | 140 |
| CO number (mg KOH/g) | n.d. | 94 |
| prim. N (g/100 g) | 0.2 | <0.1 |
| sec. N (g/100 g) | 6.47 | <0.1 |

-continued

|  | Reductively aminated polyketone (Example 2) | Quaternized product |
|---|---|---|
| tert. N (g/100 g) | 4.77 | <0.01 |
| tot. base N | 11.4 | <0.01 |
| quat. N | — | 1.1 |

Examples of use

The novel polymeric polyamines or their derivatives from Examples 5, 6, 20 or 19 were tested for the color transfer-inhibiting effect by being added to a commercial fabric softener and used to prerinse colored fabric. The fabrics were then rinsed with tapwater, dried and pressed.

The pretreated colored fabrics were then washed with white test fabrics together with a commercial detergent. The color strength of the white test fabrics was measured, comparing with the previously measured color strength, the color strength of each of the stains were determined by the method described in A. Kud, Seifen, Öle, Fette, Wachse 119, 590–594, and the color transfer-inhibiting effect was determined therefrom by the method described. The results are listed in Table 3.

The color loss on the colored fabrics was determined by determining the color strength of the fabrics before the first ash and after the 5th wash. The percentage data are (color strength before washing—color strength after the fifth ash)/color strength before washing Test conditions:
Machine: Launder-o-meter
Colored fabric: 1.0 g of colored cotton fabrics, dyeings with Direct Red 212 (3% dye on the fabric)
White fabric: 2.5 g of cotton fabric
Pretreatment:
Fabric softener: Softlan® (manufactured by Colgate-Palmolive) Polymer concentration used in the fabric softener: 2.0% Amount of fabric softener used: 1.75 g/l Temperature (rinsing): 30° C. Rinsing time: 10 min.
Washing:
Detergent: Ajax® (manufactured by Colgate-Palmolive)
Amount: 5.0 g/l
Amount of liquor: 250 g
Washing temperature: 40° C.
Water hardness: 14.5° German hardness
Ca/Mg ratio: 4.0:1.0
Washing time: 30 min.

TABLE 3

Results of tests on color transfer inhibition and reducing the color loss

| Test series | Polymer from Example | % color transfer inhibition in the 1st wash | % color removed after 5 washes |
|---|---|---|---|
| A | none | 0.0 | 30.5 |
| A | 5 | 98.0 | 7.8 |
| B | none | 0.0 | 13.3 |
| B | 6 | 84.0 | 8.7 |
| B | 20 | 93.2 | 8.7 |
| B | 19 | 93.0 | 4.0 |

The results with the polymers to be used according to the invention show that, when added to a commercial fabric softener, the polymers show a very good color transfer-inhibiting and color removal-reducing effect.

TABLE 1a

Experimental parameters

| | Polyketone | | Solvent | $NH_3$ | Catalyst | |
|---|---|---|---|---|---|---|
| Example | Mol. weight (g/mol) | Weight (g) | Amount (g) | Amount (g) | | Amount (g) |
| 2 | 2600 | 146 | THF | 4000 | 600 | $RuO_2$[1] | 8 |
| 3 | 2000 | 250 | THF | 4000 | 600 | $RuO_2$ | 8 |
| 4 | 2000 | 500 | THF | 4000 | 1200 | $RuO_2$ | 12 |
| 5 | 2000 | 1000 | THF | 4000 | 1500 | $RuO_2$ | 24 |
| 6 | 2000 | 1000 | THF | 4000 | 1200 | $RuO_2$ | 24 |
| 7 | 11,000 | 50 | THF | 1000 | 30 | $RuO_2$ | 5 |
| 8 | 10,000 | 93 | THF | 1500 | 60 | $RuO_2$ | 7 |

| | Reaction conditions | | | | Final weight | | |
|---|---|---|---|---|---|---|---|
| | Amination | | Hydrogenation | | | Final weight/ | |
| Example | t (h) | T (° C.) | t (h) | T (° C.) | p (bar) | soluble (g) | Initial weight | Yield[2] |
| 2 | 15 | 150 | 24 | 200 | 250 | 93 | 0.64 | 71.3 |
| 3 | 5 | 150 | 15 | 200 | 250 | 174 | 0.70 | 78.0 |
| 4 | 7 | 150 | 20 | 200 | 250 | 402 | 0.80 | 89.9 |
| 5 | 7 | 150 | 20 | 200 | 250 | 643 | 0.64 | 72.0 |
| 6 | 7 | 150 | 20 | 200 | 250 | 820 | 0.82 | 91.8 |
| 7 | 15 | 150 | 15 | 200 | 250 | 39 | 0.78 | 87.4 |
| 8 | 15 | 150 | 5 | 200 | 250 | 78 | 0.84 | 93.9 |

[1]$RuO_2$: $RuO_2(H_2O)_6$

[2]Yield defined as mole of product (= final weight/46) divided by mole of precursor (= initial weight/56)

TABLE 1b

Product properties

| Example | Characteristic figures | | | | | Elemental analysis | | | |
|---|---|---|---|---|---|---|---|---|---|
| | OH (mg KOH/g) | CO | prim. N (g/100 g) | sec. N | tert. N | tot. N | C | H (g/100 g) | N | O |
| 2 | 35 | 59 | 1.0 | 4.10 | 5.58 | 10.69 | 75.6 | 11.2 | 11.2 | 1.9 |
| 3 | 34 | 18 | 1.2 | 3.30 | 6.20 | 10.72 | 76.4 | 11.5 | 10.9 | 1.8 |
| 4 | n.d. | n.d. | 0.3 | 3.78 | 0.97 | 5.04 | n.d. | | | |
| 5 | 183 | <1 | 0.3 | 5.69 | 4.91 | 10.89 | n.d. | | | |
| 6 | n.d. | n.d. | 0.2 | 6.47 | 4.77 | 11.40 | n.d. | | | |
| 7 | 11 | <1 | 2.7 | 3.60 | 4.17 | 10.47 | n.d. | | | |
| 8 | <1 | <1 | 1.4 | 6.90 | 3.44 | 11.70 | n.d. | | | | n.d.: not determined

TABLE 2a

Experimental parameters

| Example | Polyketone | | Solvent | | NH₃ | Catalyst | | Reaction conditions | | | | Final weight | | |
|---|---|---|---|---|---|---|---|---|---|---|---|---|---|---|
| | Molecular weight (g/mol) | Weight (g) | | Amount (g) | Amount (g) | | Amount (g) | Amination t (h) | T (°C.) | Hydrogenation t (h) | T (°C.) | p (bar) | Final weight/ soluble (g) | Initial weight | Yield[2] |
| 9 | 2000 | 250 | THF | 1600 | 500 | Ru cat[1] | 400 | 7 | 150 | 20 | 200 | 250 | 158 | 0.63 | 70.8 |
| 10 | 2000 | 250 | THF | 1000 | 300 | Ru cat | 400 | 15 | 150 | 20 | 200 | 250 | 198 | 0.79 | 88.7 |
| 11 | 2000 | 250 | THF | 1000 | 300 | Ru cat | 400 | 15 | 150 | 20 | 200 | 250 | 197 | 0.79 | 88.3 |
| 12 | 2000 | 250 | THF | 1000 | 300 | Ru cat | 400 | 15 | 150 | 20 | 200 | 250 | 195 | 0.78 | 87.4 |
| 13 | 2000 | 168 | THF | 1500 | 25 | Ru cat | 400 | 10 | 150 | 15 | 200 | 250 | 116 | 0.69 | 77.3 |
| 14 | 2000 | 168 | THF | 1500 | 50 | Ru cat | 400 | 10 | 150 | 15 | 200 | 250 | 101 | 0.60 | 67.3 |
| 15 | 2000 | 168 | THF | 1500 | 13 | Ru cat | 400 | 10 | 150 | 15 | 200 | 250 | 108 | 0.64 | 72.0 |
| 16 | 2000 | 168 | THF | 1500 | 6.4 | Ru cat | 400 | 10 | 150 | 15 | 200 | 250 | 51 | 0.30 | 34.0 |
| 17 | 2000 | 168 | THF | 1500 | [3] | Ru cat | 400 | 10 | 150 | 15 | 200 | 250 | 61 | 0.36 | 40.7 |

[1] Ru cat.: 0.5% Ru on Al₂O₃

[2] Yield defined as mole of product (= final weight/46) divided by mole of precursor (= initial weight/56)

[3] 24 g of (NH₄)₂CO₃ in place of NH₃

TABLE 2b

Product properties

| Example | Characteristics figures | | | | | | Elemental analysis | | | |
|---|---|---|---|---|---|---|---|---|---|---|
| | OH (mg KOH/g) | CO | prim. N (g/100 g) | sec. N | tert. N | tot. N | C | H (g/100 g) | N | O |
| 9 | 18 | 93 | 0.6 | 4.30 | 1.02 | 5.90 | n.d. | | | |
| 10 | 178 | 3 | 0.3 | 6.30 | 4.51 | 11.15 | 75.5 | 11.1 | 11.7 | 1.7 |
| 11 | 201 | <1 | 0.4 | 5.40 | 5.10 | 10.93 | 75.3 | 11.1 | 11.5 | 1.7 |
| 12 | 181 | 8 | 0.4 | 6.00 | 4.45 | 10.81 | 75.5 | 11.2 | 12.0 | 1.7 |
| 13 | 46 | 10 | 0.8 | 5.80 | 3.77 | 10.40 | n.d. | | | |
| 14 | 24 | 5 | 0.6 | 5.10 | 5.04 | 10.74 | n.d. | | | |
| 15 | 49 | 20 | 0.5 | 4.70 | 4.00 | 9.16 | n.d. | | | |
| 16 | 119 | 46 | <0.1 | 3.96 | 2.71 | 6.13 | n.d. | | | |
| 17 | 182 | 94 | <0.1 | 1.49 | 1.79 | 3.28 | n.d. | | | | n.d.: not determined

We claim:

1. A polymeric polyamine comprising less than 5% by weight of carbonyl groups, based on the polymeric polyamine, obtained by reacting linear, alternating carbon monoxide/1-alkene copolymers with ammonia or amines of the formula (I)

$$R\text{—}NH_2 \qquad (I)$$

where R is —$NH_2$, —OH, $C_1$–$C_{10}$-alkyl, $C_6$–$C_{20}$-aryl, $C_7$–$C_{20}$-arylalkyl, $C_7$–$C_{20}$-alkylaryl or an organsilicon radical having 3 to 30 carbon atoms, or with a reagent which releases ammonia or the amine (I), and subsequently hydrogenating the reacted copolymers.

2. A polymeric polyamine as claimed in claim 1, wherein the 1-alkene is ethylene.

3. A polymeric polyamine as claimed in claim 1, wherein the content of chemically bonded oxygen in the polymeric polyamine is in the range from 0 to 10% by weight.

4. A polymeric polyamine as claimed in claim 1, which has a number average molecular weight Mn in the range from 100 to 1,000,000.

5. A process for preparing a polymeric polyamine which comprises less than 5% by weight of carbonyl groups, based on the polymeric polyamine, which process comprises reacting linear, alternating carbon monoxide/1-alkene copolymers with ammonia or amines of the formula (I)

$$R\text{—}NH_2 \qquad (I)$$

where R is —$NH_2$, —OH, $C_1$–$C_{10}$-alkyl, $C_6$–$C_{20}$-aryl, $C_7$–$C_{20}$-arylalkyl, $C_7$–$C_{20}$-alkylaryl or an organsilicon radical having 3 to 30 carbon atoms, or with a reagent which releases ammonia or the amine (I), and subsequently hydrogenating the reacted copolymers.

* * * * *